US 7,807,144 B2

(12) United States Patent
Yang et al.

(10) Patent No.: US 7,807,144 B2
(45) Date of Patent: *Oct. 5, 2010

(54) ORAL VACCINES

(75) Inventors: Huey-Lang Yang, Taipei (TW); John Han-You Lin, Taipei (TW); James Chein-Chih Yu, Kaohsiung (TW)

(73) Assignee: Academia Sinica, Taipei (TW)

( * ) Notice: Subject to any disclaimer, the term of this patent is extended or adjusted under 35 U.S.C. 154(b) by 734 days.

This patent is subject to a terminal disclaimer.

(21) Appl. No.: 10/969,817

(22) Filed: Oct. 21, 2004

(65) Prior Publication Data

US 2009/0317424 A1 Dec. 24, 2009

Related U.S. Application Data

(63) Continuation-in-part of application No. 09/946,273, filed on Sep. 5, 2001, now Pat. No. 6,872,386.

(51) Int. Cl.
*A01N 63/00* (2006.01)
*A61K 47/00* (2006.01)

(52) U.S. Cl. ............... 424/93.2; 424/93.1; 424/93.4; 424/93.51; 424/93.7; 424/184.1; 424/204.1; 424/234.1; 424/236.1; 424/439; 424/442

(58) Field of Classification Search .................. None
See application file for complete search history.

(56) References Cited

U.S. PATENT DOCUMENTS

| 5,830,463 A * | 11/1998 | Duke et al. ............. 424/93.51 |
| 6,248,329 B1 | 6/2001 | Chandrashekar et al. |
| 6,777,247 B2 * | 8/2004 | Lin et al. .................. 436/547 |
| 2006/0263820 A1 * | 11/2006 | Kyle ............................. 435/6 |

FOREIGN PATENT DOCUMENTS

WO    WO 01/98335    12/2001

OTHER PUBLICATIONS

Gomez-Gil et al. Applied and Environmental Microbiology, Jun. 1998, p. 2318-2322.*
Dietrich et al. Vaccine 19:2506-2512 Mar. 2001.*
Campbell et al. Fish and Shellfish Immunology (1993) 3:451-459.*
Schmidt-Nielsen et al. Animal Physiology 5th edition, 1997, p. 307 and p. 315.*
Taggart et al. Biology the unity and diversity of life, 5th edition, 1989, p. 601 table 39.4 and p. 644.*
Echinoderm (2007). In Britannica Concise Encyclopedia. Retrieved Apr. 5, 2007, from Encyclopedia Britannica Online: http://www.britanica.com/ebc/article-9363370.*
Campbell et al. Fish and Shell Fish Immunology (1993) 3, 451-459.*
Gomez-Gil et al. Applied and Environmental Microbiology, Jun. 1998, p. 2318-2322.*
Dietrich et al. Vaccine 19:2506-2512.*
Greenspan et al. (Nature Biotechnology 7: 936-937, 1999).*
Speare et al (Journal of Fish Diseases, 21(2):93-100, 1998.*
Ellis, R.W. (Chapter 29 of "Vaccines" [Plotkin, S.A. et al. (eds) published by W. B. Saunders company (Philadelphia) in 1988.*
Starr and Taggart. Biology: The Unity and Diversity of Life. Wadsworth Publishing Company, California. 1989. Chapter 6, p. 91 figure 6.6, chapter 40 p. 624-625.*
Oyster fact sheet obtained from http://www.pir.sa.gov.au/_data/assets/pdf_file/0004/33979/oyster.pdf.).*
Kentucky algae: http://bioweb.wku.edu/k12/biodiv/algae.htm.*
Parry et al. FEMS Microbiology 35:11-17, Mar. 2001.*
Wikner et al. Applied Environmental Microbiology, Jul. 1986, p. 4-8.*
Arndt et al. Hydrobiologia 255/256:231-246, 1993.*
Makridis et al. Journal of Plankton Research vol. 2 No. 11 p. 2191-2201, 1999.*
Ellis, R.W. "Vaccines" [Plotkin, S.A. et al. (eds) published by W. B. Saunders company (Philadelphia) in 1988, Chapter 29, p. 568-575.*
Koji Sode et al. "Recovery of a marine cyanobacterial recombinant product using fish-feed organisms". Marine Biotechnology 4:82-86, 1996. CP009044797.
H. Böhnel et al. "Active immunization of Black Tiger Prawn (Penaeus monodon) against vibriosis in Thailand". Berl. Münch. Tierärztl. Wschr. 112:289-295, 1999. XP009044601.
P.-J. Enzmann et al. "Development of vaccines against VHS and IHN: oral application, molecular marker and discrimination of vaccinated fish from infected populations". J. Appl. Ichthyol 14:179-183, 1998. XP09044616.
B. Noonan et al. "Recombinant Infectious Hematopoietic Necrosis Virus and Viral Hemorrhagic Septicemia Virus Glycoprotein Epitopes Expressed in *Aeromonas salmonicida* Induce Protective Immunity in Rainbow Trout (*Oncorhynchus mykiss*)". Applied and Environmental Microbiology 61(10):3586-3591, Oct. 1995. XP002087051.
P. Makridis et al. "Control of the bacterial flora of *Brachionus plicatilis* and *Artenia franciscana* by incubation in bacterial suspensions". Aquaculture 185:207-218, 2000.
G. Dietrich et al. "Gram-positive and Gram-negative bacteria as carrier systems for DNA vaccines". Vaccine 19:2506-2512, 2001.
J. Heppell et al. "Application of DNA vaccine technology to aquaculture". Advanced Drug Delivery Reviews 43:29-43, 2000.
P.H.M. Joosten et al. "Oral vaccination of juvenile carp (*Cyprinus carpio*) and gilthead seabream (*Sparus aurata*) with bioencapsulated Vibrio anguillarum bacterin". Fish & Shellfish Immunology 5:289-299, 1995.

(Continued)

*Primary Examiner*—Robert Mondesi
*Assistant Examiner*—Oluwatosin Ogunbiyi
(74) *Attorney, Agent, or Firm*—Occhiuti Rohlicek & Tsao LLP

(57) ABSTRACT

This invention features a composition that includes a multiple-cell organism for use as food for an aquatic animal (e.g., a fish or a shrimp), and a single-cell organism fed to, and as a result, bioencapsulated by, the multiple-cell organism. The single-cell organism has been transformed to express a recombinant antigen that induces an immune response in the aquatic animal.

18 Claims, No Drawings

OTHER PUBLICATIONS

Bruno Gomez-Gil et al. "Bioencapsulation of Two Different Vibrio Species in Nauplii of the Brine Shrimp (*Artemia franciscana*)". Applied and Environmental Microbiology 64(6):2318-2322, Jun. 1998.

M. Chair et al. "Accumulation of Trimethoprim, sulfamethoxazole, and N-Acetylsufamethoxazole in Fish and Shrimp Fed Medicated Artemia franciscana". Antimicrobial Agents and Chemotherapy 40(7):1649-1652, Jul. 1996.

Chien-Chih Yu et al. "Fish oral vaccine method combining bio-encapsulating and recombinant DNA technology". Institute of Bioagricultural Sciences—Academia Sinica, Taiwan and Huey-Lang Yang of Institute of Biotechnology—National Chen Kung University, Taiwan.

T. Sano. "Control of fish disease, and the use of drugs and vaccines in Japan". J. Appl. Ichthyol. 14:131-137, 1998.

K. E. Christie. "Immunization with Viral Antigens: Infectious Pancreatic Necrosis". Fish Vaccinology 90:191-199, 1997.

R. C. Palm, Jr. et al. "Specific humoral response of rainbow trout to injection immersion, and oral immunization against *vibrio anguillarum*". International Symposium on Aquatic Animal Health, Seattle, Washington. Sep. 4-8, 1994.

M. Durbin et al. "Immunization Against Furunculosis in Rainbow Trout With Iron-Regulated Outer Membrane Protein Vaccines: Relative Efficacy of Immersion, Oral, and Injection Delivery". Journal of Aqualtic Animal Health 11:68-75, 1999.

Y. Matsunaga et al. "Oral immunization with size-purified microsphere beads as a vehicle selectively induces systemic tolerance and sensitization". Vaccine 19:579-588, 2001.

R. Campbell et al. "Uptake of *Vibrio anguillarum* vaccine by *Artemia salina* as a potential oral delivery system to fish fry". Fish & Shellfish Immunology 3(6):451-459, 1993. Abstract Only.

D. J. Speare et al. "Induced resistance in rainbow trout, *Oncorhynchus mykiss* (Walbaum), to gill disease associated with the microsporidian gill parasite *Loma salmonae*". Journal of Fish Diseases 21:93-100, 1998.

R. W. Ellis, Ph.D. "New technologies for making vaccines". Vaccines Ch. 29, pp. 568-575, W. B. Saunders Company, 1988.

* cited by examiner

SEQUENCE LISTING

<160> NUMBER OF SEQ ID NOS: 2

<210> SEQ ID NO 1
<211> LENGTH: 1014
<212> TYPE: DNA
<213> ORGANISM: Nervous necrosis virus

<400> SEQUENCE: 1

```
atggtacgca aaggtgagaa gaaattggca aaacccgcga ccaccaaggc cgcgaatccg      60
caaccccgcc gacgtgctaa caatcgtcgg cgtagtaatc gcactgacgc acctgtgtct     120
aaggcctcga ctgtgactgg atttggacgt gggaccaatg acgtccatct ctcaggtatg     180
tcgagaatct cccaggccgt cctcccagcc gggacaggaa ctgacggata cgttgttgtt     240
gacgcaacca tcgtccccga cctcctgcca cgactgggac acgctgctag aatcttccag     300
cgatacgctg ttgaaacact ggagtttgaa attcagccaa tgtgccccgc aaacacgggc     360
ggtggttacg ttgctggctt cctgcctgat ccaactgaca cgaccacac cttcggcgcg      420
cttcaagcaa ctcgtggtgc agtcgttgcc aaatggtggg aaagcagaac agtccgacct     480
cagtacaccc gcacgctcct ctggacctcg tcgggaaagg agcagcgtct cacgtcacct     540
ggtcggctga tactcctgtg tgtcggcaac aacactgatg tggtcaacgt gtcggtgctg     600
tgtcgctgga gtgttcgact gagcgttcca tctcttgaga cacctgaaga gaccaccgct     660
cccatcatga cacaaggttc cctgtacaac gattccctat ccacaaatga ctccaagtcc     720
atcctcctag gatccacgcc actggacatt gcccctgatg gagcagtctt ccagctggac     780
cgtctgctgt ccattgacta cagccttgga actggagatg ttgaccgtgc tgtttactgg     840
cacctcaaga gtttgctgg aaatgctggc acacctgcag gctggtttcg ctggggcatc     900
tgggacaact tcaacaagac gttcacagat ggcgttgcct actactctga tgagcagccc     960
cgtcaaatcc tgctgcctgt tggcactgtc tgcaccaggg ttgactcgga aaac          1014
```

<210> SEQ ID NO 2
<211> LENGTH: 338
<212> TYPE: PRT
<213> ORGANISM: Nervous necrosis virus

<400> SEQUENCE: 2

```
Met Val Arg Lys Gly Glu Lys Lys Leu Ala Lys Pro Ala Thr Thr Lys
  1               5                  10                  15

Ala Ala Asn Pro Gln Pro Arg Arg Ala Asn Asn Arg Arg Arg Ser
             20                  25                  30

Asn Arg Thr Asp Ala Pro Val Ser Lys Ala Ser Thr Val Thr Gly Phe
         35                  40                  45

Gly Arg Gly Thr Asn Asp Val His Leu Ser Gly Met Ser Arg Ile Ser
     50                  55                  60

Gln Ala Val Leu Pro Ala Gly Thr Gly Thr Asp Gly Tyr Val Val Val
 65                  70                  75                  80

Asp Ala Thr Ile Val Pro Asp Leu Leu Pro Arg Leu Gly His Ala Ala
                 85                  90                  95

Arg Ile Phe Gln Arg Tyr Ala Val Glu Thr Leu Glu Phe Glu Ile Gln
            100                 105                 110

Pro Met Cys Pro Ala Asn Thr Gly Gly Tyr Val Ala Gly Phe Leu
        115                 120                 125

Pro Asp Pro Thr Asp Asn Asp His Thr Phe Gly Ala Leu Gln Ala Thr
```

-continued

```
                130                 135                 140
Arg Gly Ala Val Val Ala Lys Trp Trp Glu Ser Arg Thr Val Arg Pro
145                 150                 155                 160

Gln Tyr Thr Arg Thr Leu Leu Trp Thr Ser Ser Gly Lys Glu Gln Arg
                165                 170                 175

Leu Thr Ser Pro Gly Arg Leu Ile Leu Leu Cys Val Gly Asn Asn Thr
                180                 185                 190

Asp Val Val Asn Val Ser Val Leu Cys Arg Trp Ser Val Arg Leu Ser
                195                 200                 205

Val Pro Ser Leu Glu Thr Pro Glu Glu Thr Thr Ala Pro Ile Met Thr
    210                 215                 220

Gln Gly Ser Leu Tyr Asn Asp Ser Leu Ser Thr Asn Asp Ser Lys Ser
225                 230                 235                 240

Ile Leu Leu Gly Ser Thr Pro Leu Asp Ile Ala Pro Asp Gly Ala Val
                245                 250                 255

Phe Gln Leu Asp Arg Leu Leu Ser Ile Asp Tyr Ser Leu Gly Thr Gly
                260                 265                 270

Asp Val Asp Arg Ala Val Tyr Trp His Leu Lys Lys Phe Ala Gly Asn
                275                 280                 285

Ala Gly Thr Pro Ala Gly Trp Phe Arg Trp Gly Ile Trp Asp Asn Phe
    290                 295                 300

Asn Lys Thr Phe Thr Asp Gly Val Ala Tyr Tyr Ser Asp Glu Gln Pro
305                 310                 315                 320

Arg Gln Ile Leu Leu Pro Val Gly Thr Val Cys Thr Arg Val Asp Ser
                325                 330                 335

Glu Asn
```

ORAL VACCINES

RELATED APPLICATIONS

This application is a continuation-in-part of and claims priority to U.S. application Ser. No. 09/946,273, filed Sep. 5, 2001, now U.S. Pat. No. 6,872,386 issued Mar. 29, 2005, the contents of which are incorporated herein by reference.

BACKGROUND

There is a need for introducing a foreign protein in an aquatic animal. Such a foreign protein may lead to an efficacious immunization of aquatic animals. For example, infectious diseases are common on fish farms, due to intensive fish farming that facilitates the transmission of pathogens in an aqueous environment. Dunn et al. (1990) *Aquaculture Engineering* 9: 23. Preventing aquatic animal diseases by oral vaccination has several advantages over other methods: It is non-stressful, requires little labor, and can be applied at a large scale. However, many oral vaccines have been found ineffective as a result of failure to uptake sufficient dosage of antigen, poor antigen delivery and antigen degradation in the digestive tract.

SUMMARY

This invention relates to a novel composition, e.g., an oral vaccine useful for immunizing an aquatic animal (e.g., a fish or a shrimp), against an infectious disease (e.g., a bacterial, viral, or parasitic disease).

In one aspect, the present invention features a composition, e.g., an oral vaccine that includes a multiple-cell organism for use as food for an aquatic animal to be vaccinated, and a single-cell organism fed to, and as a result, bioencapsulated by, the multiple-cell organism. The single-cell organism has been transformed to express a recombinant antigen that can induce an immune response in the aquatic animal and thereby vaccinate the aquatic animal. The term "food" as used herein includes food (e.g., starting feed for larvae, feed additive, and artificial feed) itself and a food additive. More specifically, the single-cell organism contains a heterologous nucleic acid encoding an amino acid sequence of an antigen of interest. The nucleic acid is in a recombinant vector, which also includes one or more regulatory sequences (e.g., promoters or enhancers) operatively linked to the nucleic acid to be expressed. The antigen need not be the wild-type amino acid sequence found in a naturally occurring gene, as long as it is capable of inducing an immune response. For example, a fish oral vaccine includes *artemia* (the multiple-cell organism) that has fed on, and encapsulates *Escherichia coli* (the single cell organism), which has been transformed to express a bacterial or a viral antigen, e.g., nervous necrosis virus envelope protein, a *Photobacterium* protein, or an immunogenic fragment thereof.

In another aspect, the present invention features a method for preparing a composition, such as an oral vaccine. The method includes (1) providing a single-cell organism which has been transformed to express a recombinant antigen that can induce an immune response, either adaptive or innate immune response, in an aquatic animal and thereby vaccinate the aquatic animal, and (2) feeding the single-cell organism to a multiple-cell organism. As a result of the feeding, the multiple-cell organism (e.g., *artemia*, rotifer, algae, a *paramecium*, or an oyster embryo) bioencapsulates the single-cell organism (e.g., a bacterium or yeast). Such a multiple-cell organism can be fed to an aquatic animal as an oral vaccine.

Also within the scope of this invention is a method for orally delivering a composition, e.g., a vaccine to an aquatic animal by feeding a composition described above to the animal.

Other features, objects, and advantages of the invention will be apparent from the description and from the claims.

DETAILED DESCRIPTION

The present invention relates to a composition for delivering a foreign polypeptide to an aquatic animal. The foreign polypeptide can be any of interest. For example, it can be a therapeutic polypeptide, such as a vaccine, an immune stimulator, an antibody chain, a biologically active peptide, a cytokine or its receptors, a growth factor or its receptor, and an enzyme. One can obtain nucleotide sequences encoding these polypeptides from various public databases, e.g., GenBank and the Kabat database (Ramirez-Benitez Mdel et al., Biosystems. 2001 61:125-131).

In one embodiment, the composition is an oral vaccine for immunization of an aquatic animal against infectious diseases, either for prophylactic vaccination or for therapeutic vaccination. The oral vaccine includes a multiple-cell organism that has fed on, and therefore contains, a single-cell organism. The single-cell organism fed to the multiple-cell organism has been transformed to express a recombinant antigen that can induce an immune response in the aquatic animal. The just-described multiple-cell organism, fed to the aquatic animal, serves as an oral vaccine to the animal. In other words, an antigen, being expressed in a single-cell, multiple-cell organism or in a aquatic animal, is delivered to the aquatic animal via two steps of feeding, i.e., the above-described single-cell organism fed to the multiple-cell organism, and the multiple-cell organism from previous step fed to the aquatic animal. As a result of the delivery, the antigen can induce an immune response in the animal.

What antigen to be expressed of course depends on whether the induced immune response is against a targeted pathogen. Having the identified antigen that triggers the immune response, one can clone it into a recombinant vector that includes a nucleic acid encoding the antigen and one or more regulatory sequences operatively linked to the nucleic acid. The regulatory sequences can be those that direct constitutive expression of the antigen, as well as inducible sequences. The recombinant vector can be designed based on such factors as the single-cell organism to be transformed by it. It may contain more than one nucleic acid encoding different antigens. For example, a recombinant vector contains nucleic acids encoding two antigens, which can induce immune responses against the same or different pathogens. Alternatively, the recombinant vector may contain a nucleic acid encoding a polypeptide (e.g., a helper epitope) that is not antigenic, but itself or its encoded peptide serves to enhance an immune response against a targeted pathogen.

The just-described recombinant vector is introduced into a suitable single-cell organism via conventional transformation or transfection techniques, including a variety of art-recognized techniques for introducing a foreign nucleic acid (e.g., DNA) into a suitable host single-cell organism, e.g., calcium phosphate or calcium chloride co-precipitation, DEAE-dextran-mediated transfection, lipofection, or electroporation. Examples of suitable single-cell organisms are described, for example, in Goeddel (1990) *Gene Expression Technology: Methods in Enzymology* 185, Academic Press, San Diego, Calif. One or more just-described single-cell organisms are then fed to a suitable multiple-cell organism, a food or food additive to an aquatic animal to be vaccinated. Accordingly, the just-obtained multiple-cell organism serves as an oral vaccine, in which an antigen is in the single-cell organism that is bioencapsulated by the multiple-cell organism. Unexpectedly, such an oral vaccine has been found effective due to difficult antigen degradation in the digestive tract of the aquatic animal.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Example 1

Materials and Methods

Animals. Zebra fish, *Danio rerio*, were used. Zebra fish were kept at a suitable temperature such as 28.5° C., and reared in re-circulated, filtered water. At the start of each experiment, fish were 50 days old. Until vaccination, fish were fed with regular brine shrimp (*artemia nauplii*). After vaccination, feeding with pelleted dry food commenced amounting to 5% of fish body weight per day.

Plasmid construction and antigen preparation. *Pseudomonas aeruginosa* (PE toxin) is a bacterium that causes nosocomial infections, and has a $LD_{50}$ value (lethal dose fifty) of 1 µg for a mouse. Also recombinant *Pseudomonas* exotoxin A (PE) can elicit effective protection against native PE toxin challenge in an animal model.

Plasmid pJH4, which encodes a PE gene without a signal peptide and a c-terminal terminus, was a gift from Dr. Hwang (Hwang et al. (1987) *Cell*. 48: 129-136). The PE gene was isolated from pJH4 by digestion with EcoR I and Hind III, and the isolated PE gene was inserted into another plasmid pET24a with the same restriction enzyme cohesive ends (EcoR I and Hind III), thereby producing the plasmid pET24a-PE. The resulting plasmid was transformed into *E. coli* strain BL21(DE3). The bacteria containing the plasmid were cultured at 37° C. in LB broth with kanamycine at a concentration of 50 µg/mL. When absorbance at 600 nm reached 0.6, isopropyl-1-thio-β-D-galactoside was added to a final concentration of 1 mM. After 150 min, the bacteria were harvested, washed twice with phosphate-buffered saline (PBS), and thus, PE-enriched *E. coli* was obtained. The bacteria were kept at −20° C. until fed to *artemia*, and the expressed PE protein was analyzed by using SDS-PAGE.

PE-enriched *artemia nauplii* preparation. *Artemia nauplii* were hatched in suitable hatching condition, such as in fresh seawater at 29±1° C. or in a hatching solution (sea water:fresh water/2:1) at 25° C., under continuous light and sufficient air. More specifically, four grams of *Artemia* eggs (INVE *Artemia* cysts, Belgium) were suspended in fresh water for 30 minute. They were then transferred to 5 liters of the just-described hatching solution and incubate at 25° C. with gentle aeration for up to 24 hours until *Artemia* larva hatched. Forty hours after hatch, *artemia* were collected and fed with PE-enriched *E. coli* (or *E. coli* control). The larva were resuspended in seawater to a density of 500 larvae/ml and cultured with aeration until they were ready to eat bacteria. To feed them with bacteria, a concentrated stock solution of desired bacteria was added to the *Artemia* culture to a concentration of 108 bacteria/ml. The resultant mixture was further cultured with gentle aeration at 25° C. for 120 minutes. After feeding, *artemia nauplii* were collected, and washed five times with PBS. *Artemia nauplii* were fed to zebra fish immediately, or kept at −20° C. for subsequent use or analysis.

SDS-PAGE electrophoresis and western blotting. Total protein from an *artemia* sample was quantified by Protein Assay Kit (BIO-RAD, 2000 Alfred Nobel Drive, Hercules, Calif.) and PE protein in an *artemia* sample was analyzed by using SDS-PAGE and western blot. The sample was homogenized in Laemmli buffer (Laemmli, U. K. (1970) *Nature* (London) 227: 650-685), and boiled for 5 minutes. The PE protein was analyzed by 8% polyacrylamide gels containing SDS (SDS-PAGE), and stained with Coomassie blue after electrophoresis. It was more than 40% in the total *E. coli*-expressed proteins. In an immunoblotting assay, the PE protein in the sample was electrophoresed on gels, transferred to a nitrocellulose paper; incubated with the rabbit anti-PE antibody and a second antibody (goat anti-rabbit conjugated with alkaline phosphatase), and then stained with an alkaline phosphatase substrate (BIO-RAD). Procedures were carried out under conditions recommended by the supplier (BIO-RAD). The anti-PE antibody was generated in rabbits by immunization. 250 µg of the PE protein emulsified in Freund's complete adjuvant was administered to the rabbits. The pooled rabbit-anti-PE antibody fractions were prepared for western blotting analysis.

Vaccination schedule. PE-enriched *artemia nauplii* were fed to zebra fish that have been starved for 24 hours before vaccination. During feeding, the water flow was stopped. Fish were fed four times a day. Control fish (non-vaccinated fish) were fed with control *artemia nauplii*. After 6 weeks, both vaccinated and non-vaccinated fish were fed with pelleted dry food. After 3 weeks, fish were challenged with a PE toxin (Sigma)

Challenge test with PE toxin. In order to determine $LD_{50}$ values of PE in zebra fish, five experimental groups (six non-vaccinated fish each) were tested. Five groups were starved for 24 hours, anaesthetized by using 200 ppm of 2-phenoxyethanol, and intraperitonally injected with 0, 0.5, 1, 1.5 and 2 µg of the PE toxin, respectively. A $LD_{50}$ value of PE for zebra fish was thus determined at the range of 1-1.2 µg in 50 days old zebra fish. In a subsequent experiment, vaccinated fish were challenged with 1.2 µg of the PE toxin.

Immunohistochemistry study of uptake of PE in fish. After feeding with the enriched *artemia nauplii*, six groups (three fish each) were killed at the time 0, 1, 2, 3, 6, and 12 hours, respectively, and put on ice for 1 minute. Fish was dissected, fixed in 4% formalin overnight, and after rinsing with PBS and dehydration, embedded in paraffin wax. Continuous sections were cut, mounted on poly-L-lysine treated slides, and incubated with a 3% $H_2O_2$-containing PBS solution to inactivate endogenous peroxidase. The slides were then rinsed with PBS-E (PBS with 1 mM EDTA and dehydrated with 50% (v/v, 50% ethanol and 50% water) and 90% ethanol (v/v, 90% ethanol and 10% water). The PE protein was detected by an immunoperoxidase reaction using rabbit-anti-PE serum (1:1000) and a goat-anti-rabbit horseradish peroxidase (HRP) conjugate (1:200). Conjugates were visualized with a HRP substrate (0.012% v/v hydrogen peroxide in water) and chromogen (0.4 mg/mL). After aminoethylcarbazole was applied to the sections for 15 minutes, the slides were washed twice with PBS-E. The sections was counterstained with acid hematoxylin for 5 minutes, blued with aqueous ammonia for 1 min, and then rinsed with PBS. Detection was carried out by using water as mounting medium, and slides were viewed under a microscope at a magnification of 40-400×. Tissues containing the recombinant PE were stained as reddish-brown color.

Results

Determination of $LD_{50}$. Since the weight of zebra fish varies even at same age, the $LD_{50}$ value of the PE toxin for 50 days old zebra fish was determined to be between 1 to 1.2 µg and $LD_{50}$ dose of 1.2 µg per fish was used as the challenge dose. To confirm the $LD_{50}$, twenty-one non-vaccinated fish were challenged by intraperitonal injections. Ten fish (50%) died within a week, within this group, 7 fish (33%) died between 2 to 3 days. Further, more than 80% of fish had symptoms of hemorrhage, as observed on fish skin and adipose tissues. All of the fish had lost appetite for a period up to 7 to 10 days after the injections. However, control fish, intraperitonally injected with PBS, had no symptoms of hemorrhage and lost appetite for only one day.

The efficacy of an oral vaccine. Sixteen fish vaccinated by feeding oral vaccine were challenged by intraperitonal injections of 1.2 µg PE toxin. Four vaccinated fish (mortality rate is 25%) died within 5 days. For comparison, among the six fish in the non-vaccinated group (mock vaccination groups with *artemia* fed with regular *E. coli*), four fish died within 5 days (mortality rate is 75%). The results show that the oral vaccine containing the recombinant *E. coli* bioencapsulated by *artemia* is efficacious. Further, the vaccinated fish also lost appetite, but they recovered 2 to 3 days earlier than those fish survived from PE challenge in the non-vaccinated group.

The optimal time of preparation enriched *artemia nauplii*. To evaluated the optimal time of prepare enriched *artemia*, the *E. coli* (BL21, DE3) that expressed PE protein was fed to *artemia nauplii*. The *artemia nauplii* were killed at time 0, 15, 30, 45, 60, 90, and 120 minutes after feeding, and washed five times with PBS to eliminate the superficially attached *E. coli*. The *artemia nauplii* samples were suspended in 6 M urea and sonicated. The PE protein extracted from the samples were analyzed by SDS-PAGE and detected by western blotting analysis with rabbit-anti-PE antibody (see above). The results show that the amount of the PE protein in *artemia nauplii* increases after feeding, reaches a plateau after 30 to 60 minutes, and drops later on. Accordingly, the optimal time for feeding *artemia nauplii* in this exampled experiment is 45 minutes.

Comparison of recombinant and bacterial native antigens. Six strains of *Pseudomonas aeruginosa* (ATCC 15693, ATCC 29260, ATCC 33449, ATCC 33354, ATCC 33355 and ATCC 33359) that conferred PE toxin and PE-enriched *E. coli* recombinant were individually fed to *artemia nauplii*. PE proteins extracted from seven *artemia nauplii* samples were analyzed by SDS-PAGE and detected by western blotting analysis with rabbit-anti-PE antibody (see above). *Artemia* fed with PE-enriched *E. coli* recombinant contained PE protein that can be easily observed by the PAGE gel analysis but those *artemia* fed with six strains of *Pseudomonas aeruginosa* did not show any PE protein detectable in PAGE gel analysis. The results indicated that the feeding of recombinant *E. coli* with specific antigen did increase the amount of antigen as compared to the prior art that fed *artemia* with intact bacterial pathogen. See Gomez-Gil et al. (1998) *Appl Environ Microbiol* 64: 2318-2322. Thus, fish can easily get sufficient PE protein to trigger an immune response after uptake of an oral vaccine containing the recombinant PE-enriched *E. coli* bioencapsulated by *artemia nauplii.*

The uptake of the PE protein in fish intestine. Histological observation aided by immuno-assay with anti-PE antibody indicated that in a period of one to three hours after feeding with *artemia nauplii*, the PE protein was observed in the lumen of the fish intestine, and the uptake reached the maximal amount in two hours after feeding. Data show that particles of the PE protein were found to pass the mucosal and enter the epithelial cell. The particles began to disappear after six hours, and totally disappeared after 12 hours.

The safety of the oral vaccine of this invention was also evaluated. No abnormality was observed in the morphology, appetite, swimming behavior, or death in all fish fed with the oral vaccine.

Example 2

The $LD_{50}$ of *Pseudomonas aeruginosa* on Zebra Fish was determined. More specifically, *Pseudomonas aeruginosa* (ATCC 15692) and *E. coli* were separately incubated in LB at 26° C. for 18 hours and at 37° C. for 16 hours, respectively. The bacterial cells were harvested by centrifugation and washed twice with phosphate buffered saline (PBS) to remove residual growth medium and cell secretion. They were then resuspended in PBS and adjusted to $2.5\times10^{10}$ cells/ml. Six Zebra fish were injected with *Pseudomonas aeruginosa* at a dose of 10 μl ($2.5\times10^{8}$ cells) per fish. Another six Zebra fish were injected with the same dose of *E. coli*. After the injection, all fish were observed for up to 6 days. Six hours after the injection, those fish injected with *Pseudomonas aeruginosa* begun to slow down. Meanwhile, hemorrhages appeared on the abdominal surface and two sides of the body. These fish died 12 hours after the injection. They all showed typical symptoms of *Pseudomonas* symptom infection, e.g., lose of appetite and hemorrhages in the epidermal layer of abdomen tissues. In contrast, those fish injected with *E. coli* did not show any abnormal swimming behavior or hemorrhages and remained alive during the same period. This observation indicates that *Pseudomonas aeruginosa* is a pathogen or opportunist pathogen in fish.

Further, 30 zebra fish were divided into five groups, six in each group. They were injected with 10 μl PBS containing 0, $5\times10^{6}$, $5\times10^{7}$, $5\times10^{8}$, and $5\times10^{9}$ *Pseudomonas aeruginosa*, respectively, and observed for 48 hours. The mortalities of the groups were then determined and summarized in Table 1 below.

TABLE 1

The determination of $LD_{50}$ of *Pseudomonas aeruginosa* on Zebra Fish

| Number of bacteria/infection/fish | Mortality in 48 hours |
|---|---|
| $5\times10^{9}$ | 100% |
| $5\times10^{8}$ | 83% |
| $5\times10^{7}$ | 50% |
| $5\times10^{6}$ | 16% |
| PBS | 0 |

The results indicate that the LD50 is $5\times10^{7}$ *Pseudomonas aeruginosa* per infection per fish.

Then, the efficacy of the oral vaccine described there in was tested in *Pseudomonas*-challenged zebra fish. *Artemia nauplii* fed with PE-enriched *E. coli* and PE-free *E. coli* were prepared according to the method described above. Forty-five and twenty zebra fish were fed with the two types of *Artemia nauplii* twice a day at an eight-hour interval, respectively. One month later, the Zebra fish in these two groups, i.e., Vaccinated and Control Groups, were challenged by injection of 10 μl PBS containing $5\times10^{7}$ live *Pseudomonas aeruginosa*. After six days, the mortalities of the groups were determined and summarized in Table 2 below.

TABLE 2

Effects of Vaccination on Zebra fish

| Groups | Number of Fish | Mortality | Protection rate (1- Mortality)% |
|---|---|---|---|
| Control Group | 20 | 9/20 (45%) | 55% |
| Vaccinated Group | 45 | 10/45 (22%) | 78% |

As shown in Table 2, *Pseudomonas aeruginosa* infection caused 45% mortality in the fish not vaccinated. In contrast, only 22% of the vaccinated fish died with 6 days after the infection. These results indicate that the oral vaccine of this invention protects fish from *Pseudomonas aeruginosa* infection. The relative percentage of protection or Relative Percent Survival (RPS) was calculated to be 51% RPS was determined by the formula: Relative Percent Survival=1−(% mortality in vaccinated group/% mortality in control group (Jarp, A. Tverdal in Statistical aspects of fish vaccination trails, Fish vaccinology, Dev. Biol. Stard. Basel, Karger, 1997 Vol 90, pp. 311-320.)

Example 3

It is known that nervous necrosis virus (NNV), a major fish pathogen, often causes 99% of mortality. *Artemia* fed with *E. coli*. containing a vector that encoded a subunit gene of NNV envelope protein was used to introduce the protein in fish and induce immune response, thereby protecting the fish.

The amino acid sequence and nucleotide sequences of this NNV envelope protein are shown below.

```
                                             (SEQ ID NO: 2)
MVRKGEKKLAKPATTKAANPQPRRRANNRRRSNRTDAPVSKASTVTGFGR

GTNDVHLSGMSRISQAVLPAGTGTDGYVVVDATIVPDLLPRLGHAARIFQ

RYAVETLEFEIQPMCPANTGGGYVAGFLPDPTDNDHTFGALQATRGAVVA

KWWESRTVRPQYTRTLLWTSSGKEQRLTSPGRLILLCVGNNTDVVNVSVL

CRWSVRLSVPSLETPEETTAPIMTQGSLYNDSLSTNDSKSILLGSTPLDI

APDGAVFQLDRLLSIDYSLGTGDVDRAVYWHLKKFAGNAGTPAGWFRWGI

WDNFNKTFTDGVAYYSDEQPRQILLPVGTVCTRVDSEN (SEQ ID NO: 1)
atggtacgcaaaggtgagaagaaattggcaaaacccgcgaccaccaaggc cgcgaatccgcaaccccgccgacgtgctaacaatcgtcggcgtagtaatc gcactgacgcacctgtgtctaaggcctcgactgtgactggatttggacgt gggaccaatgacgtccatctctcaggtatgtcgagaatctcccaggccgt cctcccagccgggacaggaactgacggatacgttgttgttgacgcaacca tcgtccccgacctcctgccacgactgggacacgctgctagaatcttccag cgatacgctgttgaaacactggagtttgaaattcagccaatgtgcccgc aaacacgggcggtggttacgttgctggcttcctgcctgatccaactgaca acgaccacaccttcggcgcgcttcaagcaactcgtggtgcagtcgttgcc aaatggtgggaaagcagaacagtccgacctcagtacaccgcacgctcct ctggacctcgtcgggaaggagcagcgtctcacgtcacctggtcggctga tactcctgtgtgtcggcaacaacactgatgtggtcaacgtgtcggtgctg tgtcgctggagtgttcgactgagcgttccatctcttgagacacctgaaga gaccaccgctcccatcatgacacaaggttccctgtacaacgattccctat ccacaaatgactccaagtccatcctcctaggatccacgccactggacatt gcccctgatggagcagtcttccagctggaccgtctgctgtccattgacta cagccttggaactggagatgttgaccgtgctgtttactggcacctcaaga agtttgctggaaatgctggcacacctgcaggctggtttcgctggggcatc tgggacaacttcaacaagacgttcacagatggcgttgcctactactctga tgagcagccccgtcaaatcctgctgcctgttggcactgtctgcaccaggg ttgactcggaaaac.
```

The experiment was conduced in the same manner described above except that the gene encoding the NNV envelope protein was cloned into a pET24a-BL21 (DE3) expression vector. Recombinant *E. coli* bacteria transformed with the vector were treated with formalin before being fed to Grouper (Grouper, *Epinephelus* sp.). The LD50 was determined in the same manner described above except that grouper larva (*Epinephelus coiodes*) that were 1.5 cm in length (around post hatch 35 days) were used. The LD50 was determined to be $1\times10^5$ TCID50.

Forty Grouper (*Epinephelus coiodes*) fry were divided into two groups (20 in each). The fry in one group were fed twice each day for consecutive two days with *Artemia* containing *E. coli* BL21(DE3) ("mock group"). Those in the other group were fed in the same manner with *Artemia* containing *E. coli* BL21(DE3) that contained a pET24a-NNV plasmid and expressed the NNV envelope protein ("vaccinated group"). Seven days later, all fish were challenged with NNV at LD50 by injection, and then observed for eight weeks. It was found that, in the vaccinated group, sixteen fish survived (a survival rate of 80%); and only nine fish survived (a survival rate of 45%) in the mock group (See Table 3). The RPS was calculated to be 64%. This result indicates that a single feeding period was sufficient to protect grouper fry from the lethal NNV infection.

TABLE 3

Effects of NNV oral vaccine on NNV-challenged zebra fish

| Test group | Cumulative mortality | Protection rate (1- Mortality)% |
|---|---|---|
| Mock vaccinated group | 55% (11/20) | 45% |
| Vaccinated group | 20% (4/20) | 80% |

Other Embodiments

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, an oral vaccine as described above is used for immunization of other domestic animals (e.g., pigs and chickens) or humans. Thus, other embodiments are also within the claims.

What is claimed is:

1. A composition, comprising:
a bioencapsulating organism which is *Artemia*, rotifer, alga, or paramecium for use as food for a fish; and
a single-cell organism fed to, and bioencapsulated by, the bioencapsulating organism;
wherein the single-cell organism is a bacterium or yeast that is transformed and expresses a recombinant antigen,
wherein the antigen induces an immune response in the fish against an infectious disease caused by *Pseudomonas aeruginosa* or nervous necrosis virus, and
wherein the antigen is *Pseudomonas* exotoxin A or nervous necrosis virus envelope protein.

2. The composition of claim 1, wherein the bioencapsulating organism is *Artemia*.

3. The composition of claim 2, wherein the single-cell organism is a bacterium.

4. The composition of claim 3, wherein the single-cell organism is *Escherichia coli* or *Vibrio*.

5. The composition of claim 1, wherein the recombinant antigen is nervous necrosis virus envelope protein.

6. The composition of claim 1, wherein the recombinant antigen is *Pseudomonas* exotoxin A.

7. The composition of claim 4, wherein the recombinant antigen is *Pseudomonas* exotoxin A.

8. The composition of claim 4, wherein the recombinant antigen is nervous necrosis virus envelope protein.

9. A method for preparing the composition of claim 1, comprising:

providing a single-cell organism which is a bacterium or yeast that has been transformed to express a recombinant antigen that induces an immune response in a fish against an infectious disease caused by *Pseudomonas aeruginosa* or nervous necrosis virus; and
feeding the single-cell organism to a bioencapsulating organism which is *Artemia*, rotifer, alga, or paramecium to obtain a composition containing the bioencapsulating organism that bioencapsulates the single-cell organism
wherein the recombinant antigen is *Pseudomonas* exotoxin A or nervous necrosis virus envelope protein.

10. The method of claim 9, wherein the bioencapsulating organism is *Artemia*.

11. The method of claim 10, wherein the single-cell organism is a bacterium.

12. The method of claim 11, wherein the single-cell organism is *Escherichia coli* or *Vibrio*.

13. The method of claim 12, wherein the recombinant antigen is nervous necrosis virus envelope protein.

14. The method of claim 12, wherein the recombinant antigen is *Pseudomonas* exotoxin A.

15. A method for orally delivering the composition of claim 1, comprising:
feeding a bioencapsulating organism which is *Artemia*, rotifer, alga, or paramecium to a fish to be vaccinated,
wherein the bioencapsulating organism bioencapsulates a single-cell organism which is a bacterium or yeast that has been transformed to express a recombinant antigen, which induces an immune response in the fish against an infectious disease caused by *Pseudomonas aeruginosa* or nervous necrosis virus, and wherein the antigen is *Pseudomonas* exotoxin A or nervous necrosis virus envelope protein.

16. The method of claim 15, wherein the single-cell organism is *Escherichia coli* or *Vibrio* and the bioencapsulating organism is *Artemia.*

17. The method of claim 16, wherein the recombinant antigen is nervous necrosis virus envelope protein.

18. The method of claim 16, wherein the recombinant antigen is *Pseudomonas* exotoxin A.

* * * * *